United States Patent
Shimoji

(10) Patent No.: US 6,440,122 B1
(45) Date of Patent: Aug. 27, 2002

(54) METHOD OF USING A CORDLESS PUMPED μ-CHIP MEDICAL LASER TO CURE COMPOSITES

(76) Inventor: Yutaka Shimoji, 2125 University Ct., Clearwater, FL (US) 33764

( * ) Notice: Subject to any disclaimer, the term of this patent is extended or adjusted under 35 U.S.C. 154(b) by 0 days.

(21) Appl. No.: 09/475,851

(22) Filed: Dec. 30, 1999

Related U.S. Application Data

(60) Division of application No. 09/107,623, filed on Jun. 30, 1998, now Pat. No. 6,099,520, which is a continuation-in-part of application No. 08/872,085, filed on Jun. 10, 1997, now Pat. No. 5,928,220.

(51) Int. Cl.[7] ............................................. A61B 18/18
(52) U.S. Cl. ................................................ 606/2; 606/3
(58) Field of Search ............................. 606/2, 3, 8–10, 606/13–18; 607/89–90, 93, 94; 433/215–216

(56) References Cited

U.S. PATENT DOCUMENTS

| | | | | |
|---|---|---|---|---|
| 5,233,283 A | * | 8/1993 | Kennedy | 320/13 |
| 5,272,716 A | * | 12/1993 | Soltz et al. | 372/109 |
| 5,616,141 A | * | 4/1997 | Cipolla | 606/15 |

* cited by examiner

*Primary Examiner*—Linda C. M. Dvorak
*Assistant Examiner*—Pete J Vrettakos

(57) ABSTRACT

A controlled process for thoroughly curing light-activated surgical and dental composites is presented using a hand-held, self-contained, cordless, rechargeable laser instrument. At least one micro laser generates focused single wavelength blue laser light of at most 480 nm, and enhances efficiency and control of curing. The process of use includes switching from stand-by mode to curing mode of operation of the instrument to save time during surgical and dental procedures.

8 Claims, 1 Drawing Sheet

METHOD OF USING A CORDLESS PUMPED µ-CHIP MEDICAL LASER TO CURE COMPOSITES

RELATED PATENT CROSS REFERENCE

This is a division of co-pending U.S. patent application Ser. No. 09/107,623 entitled "Method of Using a Cordless Medical Laser to Cure Composites and Sterilize Living Tissue", filed on Jun. 30, 1998, now U.S. Pat. No. 6,099,520 which is a continuation-in-part of U.S. Pat. Ser. No. 08/872, 085 now U.S. Pat. No. 5,928,220 entitled "Cordless Dental and Surgical Laser", filed on Jun. 10, 1997.

BACKGROUND

The present invention relates to a method of using a medical laser instrument for curing dental and surgical composite materials, which provides single line laser light generation from diode pumped solid state microchips.

Cipolla discloses in U.S. Pat. No. 5,616,141 an argon laser dental instrument and method for curing dental composites. However, the laser light consists of multi-line bands of wavelength, of which some wavelength lines must be filtered, since they are not useful for the purpose of curing. Therefore, the system displays an inefficient way of producing the laser line necessary for the curing. In addition, the laser system is an argon gas laser for which a high power cooling system must be supplied in order to operate it. Furthermore, the argon gas laser requires high voltage and a high current power source. Therefore, the instrument can not be made into a compact, hand-held, self-contained unit. A large stationary unit is required to be connected to a separate hand-held portion by optic fibers and cables. Furthermore, the output of the argon laser consists of many lines of wavelength from blue to green of which only the blue line of 488 nm is useful for curing. The beam is collimated and, therefore, has constant power along the propagation length of the beam. This results in uncontrolled curing and air bubble entrapment due to the fact that the surface layers begin to cure prior to the deeper layers.

Also disclosed is a dual wavelength laser in U.S. Pat. No. 5,507,739 for dental therapy, but these are 1.06 µ, and 1.32 µ infrared wavelengths which are not useful for curing composites nor for sterilization of tissue.

Kowalyk et al. discloses a method for removing tooth decay in U.S. Pat. No. 5,456,603 using pulsed, frequency doubled lasers emitting red, green, deep blue, and UV light attenuated by some dye material. Consequently, none of wavelengths described in the patent match the maximum absorption wavelength of medical composites for curing. The device is not a compact, hand-held, self-contained instrument.

Therefore, there remains a need to provide an efficient method for laser curing of dental and surgical composite materials in a cordless, portable, self-contained, hand-held instrument which generates a single, optimum wavelength.

SUMMARY

An object of the present invention is to provide a practical and efficient method for curing medical composites with laser light.

Another object of the invention is to provide a method of curing medical composite materials that overcomes the problems of incomplete curing of the prior art.

These and other objects are achieved in the present inventive method of use of a cordless medical laser by generating and focusing a single line wavelength laser light from a hand-held, self-contained, diode pumped, solid state laser instrument. Dental or surgical composites are cured by a focused, Q-switched, pulsed wavelength of laser light matching the optimum absorption wavelength of the composite material used. The focal point is moved through the composite from the deep layers to the surface to ensure complete curing.

These and other objects and advantages of the present invention will become more apparent from the following drawing and the description of preferred embodiments.

DESCRIPTION OF PREFERRED EMBODIMENT

Figure 1:
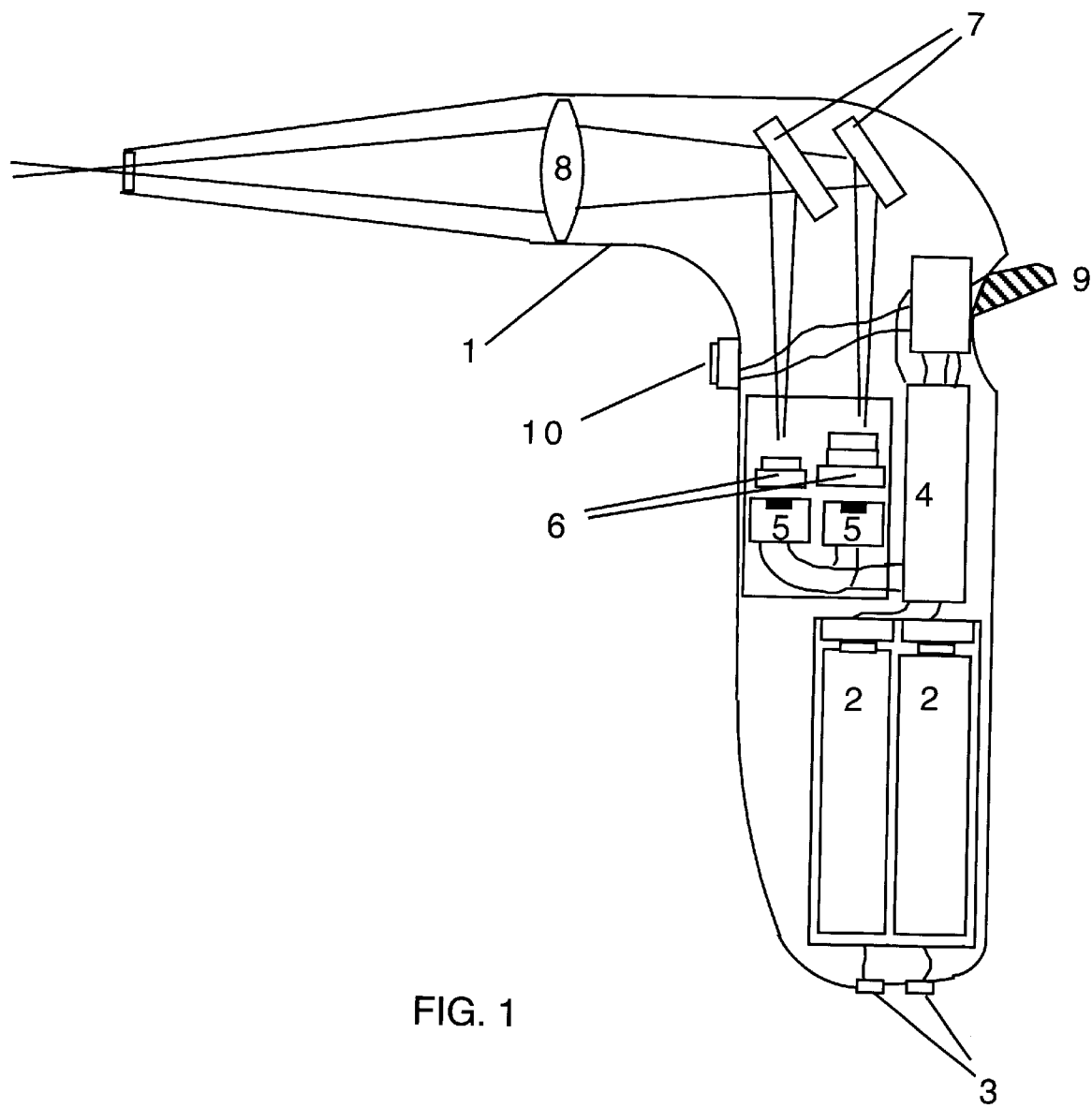
FIG. 1 is a longitudinal cross sectional view of the medical laser instrument used in the method of the present invention showing two different diode pumped solid state microchip lasers for curing composites.

The present invention is a method for curing surgical and dental composites using a hand-held, cordless, portable, self-contained laser instrument such as the one shown in FIG. 1. First a living biological tissue site is exposed so that directed laser light can illuminate the site. The microchip 6 crystal laser materials may be optically contacted, bonded by thermal diffusion or bonded by optical epoxy. The solid state microchip 6 of the present invention is a solid state laser crystal material fabricated to have a volume of less than 1 cubic centimeter. A microchip 6 can consist of several such crystal materials all contained within the optical cavity. For the curing mode of operation, a sufficient quantity of a chosen photo-polymerizable medical composite material is placed at a site of repair and restoration. A switching means 9 just above the on/off switch 10 activates pumping from a first to at least a second chosen solid state laser microchip 6 to generate a selected wavelength of at most 480 nm. The wavelength is selected to be the maximum absorption wavelength of the material to be cured. The beam is focused through a lens 8 after being reflected from turning mirrors 7. A first microchip 6 in this example is Nd:YAG/KNbO$_3$ and a second is Nd:YVO$_4$/KNbO$_3$. The focused beam is directed into the chosen composite light activated material for a sufficient time for curing to occur. The power consumption during laser operation is at most 10 watts, and the maximum laser output power is at least 20 m Watts. The output power is adjusted to the requirements of the targeted material by the diode laser driver electronics 4.

To enhance the completeness of curing, the focal point of the laser light is placed on the tissue/composite interface first, and then moved through the composite material to the surface, which is distal to the above interface. This eliminates air bubble entrapment and it enhances the bond between the composite material and the biological tissue to be repaired.

Since only one line of wavelength of laser light is generated by the microchip 6, no filters are needed and the power is used much more efficiently than in the prior art. So little power is required, that all of the components of the instrument 1 including the rechargeable batteries 2 with recharging electrodes 3, diode laser driver electronics 4, pumping diode lasers 5, microchips 6, mirrors 7, and lens 8 are housed in a unit hand-held, ergonomic, cordless, self-contained, portable, light-weight instrument housing, which has not been possible in the prior art. The microchips 6 are constructed out of any suitable lasing material not limited to solid state materials.

Q-switched, pulsed laser light is provided to further enhance efficiency and control of the curing process. A focused beam is superior to a collimated beam for curing due to the fact that light activation of deeper layers of photo-polymerizable medical composite material can be accomplished before the surface layer is cured. The switch 9 ensures that only one microchip will be engaged at one time. This combined use saves a great deal of time in surgical and dental procedures.

Accordingly, for all these reasons set forth, it is seen that the method of the present invention represents a great advancement in the art of composite curing in surgery and dentistry, and has substantial commercial merit.

While there is shown and described herein certain specific process steps and methods, it will be manifest to those skilled in the art that modifications may be made without departing from the spirit and scope of the underlying inventive concept. The present invention shall not be limited to the particular process steps and methods herein described except by the scope of the appended claims.

What is claimed is:

1. A process of curing photo-polymerizable medical composite materials comprising the steps of:

placing a quantity of a chosen photo-polymerizable medical composite material at a site of repair, said quantity being sufficient to effect repair;

generating and focusing a single band blue wavelength laser light of a selected wavelength from inside a hand-held, self-contained, diode pumped solid state laser generation instrument by pumping at least one chosen solid state microchip by at least one diode laser and by passing the laser light generated from said microchip through a focusing lens, said hand-held, self-contained instrument contains said diode laser housed together with said at least one chosen solid state laser microchip and with a rechargeable diode laser power supply and with a switch for firing said laser;

directing a focused said blue wavelength laser light from said instrument into said material for a sufficient time to effect curing of said material, the wavelength of said laser light being at most 480 nm, and said wavelength being selected to be a maximum absorption wavelength of said chosen material.

2. The process according to claim 1 wherein said wavelength is 437 nm.

3. The process according to claim 2 wherein the step of directing said laser light into said material is accomplished by first placing the focal point of said focused laser light at a biological tissue interface with said material, and then by moving said focal point from said interface in a direction toward the surface of said material distal to said interface and by ending at said surface distal to said interface, such that said material is cured at said interface initially and at said surface lastly.

4. The process according to claim 1 wherein said wavelength is 457 nm.

5. The process according to claim 4 wherein the step of directing said laser light into said material is done by first placing the focal point of said focused laser light at a biological tissue interface with said material, and then by moving said focal point from said interface in direction toward the surface of said material distal to said interface and by ending at said surface distal to said interface such that said material is cured at said interface initially and at said surface lastly.

6. The process according to claim 1 wherein the step of generating said laser light is done by generating a Q-switched, pulsed laser light, a maximum power of said laser light being adjustable to requirements of said material.

7. A method for curing medical composite having a light activated cure mechanism comprising the step of directing a beam of focused, Q-switched, pulsed laser light into said composite such that curing of said composite is accomplished, said laser light being generated at a selected single band blue wavelength from at least one laser material, said at least one laser material being housed inside a hand-held, self-contained instrument together with a rechargeable laser power supply and with a switch for firing said laser, said wavelength being at most 480 nm, said wavelength being selected to be a maximum absorption wavelength of said composite.

8. The method according to claim 7 wherein said laser material is a solid state crystal microchip, said microchip is pumped by a diode laser, a maximum power of said laser light being adjustable to requirements of said composite.

\* \* \* \* \*